United States Patent [19]
Frassica et al.

[11] Patent Number: 5,667,476
[45] Date of Patent: Sep. 16, 1997

[54] ENDOSCOPE ARTICULATION SYSTEM TO REDUCE EFFORT DURING ARTICULATION OF AN ENDOSCOPE

[75] Inventors: James J. Frassica, Chelmsford; Robert E. Ailinger, Norwood, both of Mass.

[73] Assignee: Vision-Sciences, Inc., Natick, Mass.

[21] Appl. No.: 464,260

[22] Filed: Jun. 5, 1995

[51] Int. Cl.[6] ........................................... A61B 1/00
[52] U.S. Cl. ................ 600/149; 600/146; 600/147; 600/148; 600/150; 600/139
[58] Field of Search ..................... 600/139, 141, 600/142, 145, 146, 147, 148, 149, 150, 151

[56] References Cited

U.S. PATENT DOCUMENTS

| | | | |
|---|---|---|---|
| 2,975,785 | 3/1961 | Sheldon | 128/6 |
| 3,788,303 | 1/1974 | Hall | 128/4 |
| 4,375,818 | 3/1983 | Suwaki et al. | 128/660 |
| 4,461,282 | 7/1984 | Ouchi et al. | 128/4 |
| 4,633,882 | 1/1987 | Matsuo et al. | 128/660 |
| 4,646,722 | 3/1987 | Silverstein et al. | 128/4 |
| 4,688,555 | 8/1987 | Wardle | 600/149 |
| 4,742,816 | 5/1988 | Suzuki et al. | 128/4 |
| 4,825,850 | 5/1989 | Opie et al. | 128/4 |
| 4,941,455 | 7/1990 | Watanabe et al. | 600/146 |
| 4,947,827 | 8/1990 | Opie et al. | 128/4 |
| 4,996,974 | 3/1991 | Ciarlei | 600/149 |
| 5,376,094 | 12/1994 | Kline | 606/113 |
| 5,388,568 | 2/1995 | van de Heide | 600/146 |

FOREIGN PATENT DOCUMENTS 2 138 687 A   10/1984   United Kingdom ............. A61B 1/00

*Primary Examiner*—Beverly M. Flanagan
*Attorney, Agent, or Firm*—Seed and Berry LLP

[57] ABSTRACT

An endoscope having an articulation system that provides a mechanical advantage and facilitates articulation of the distal section of the endoscope insertion tube. The endoscope includes a handle held by a user during an endoscopic procedure and an insertion tube attached at its proximal section to the handle. A plurality of control cables extending the length of the insertion tube are securely attached to the insertion tube's distal section and are axially movable to articulate the distal section. Control wheels are rotatably attached to the handle and positioned to be manipulated by the user during the endoscopic procedure. The articulation system is connected at one end to the control cables and at the other end to the control wheels. The articulation system transmits movement of the control wheels to the control cables. The articulation system is partially linearly movable between the control wheels and the control cables upon movement of at least one control wheel so as to provide a mechanical advantage in converting force from the control wheel to the control cable. The articulation system is configured with approximately a two-to-one mechanical advantage, such that a force exerted on the control wheel is approximately one-half of the force that is transmitted to the control cable to move the control cable axially, thereby articulating the insertion tube's distal section.

18 Claims, 4 Drawing Sheets

5,667,476

ENDOSCOPE ARTICULATION SYSTEM TO REDUCE EFFORT DURING ARTICULATION OF AN ENDOSCOPE

TECHNICAL FIELD

The present invention relates to the field of endoscopy, and more particularly, to a system for articulation of an endoscope.

BACKGROUND OF THE INVENTION

The use of endoscopes for diagnostic and therapeutic indications is rapidly expanding. To improve performance, specialized endoscopes have been developed for specific uses. For example, there are upper endoscopes for examination of the esophagus, stomach, and duodenum, colonoscopes for examining the colon, angioscopes for examining blood vessels, bronchoscopes for examining the bronchia, laparoscopes for examining the peritoneal cavity, and arthroscopes for examining joint spaces. The discussion which follows applies to all of these types of endoscopes and any modifications thereof.

There has been a large increase in the use of endoscopes for screening symptomatic and asymptomatic patients. These endoscopes are expensive and are used in contaminated and sensitive environments. Conventional endoscopes typically have an elongated insertion tube that is inserted into a patient at a point of entry and extended to a selected body cavity. The insertion tube is connected at its proximal end to a handle portion. The distal end of the insertion tube is controlled and steered by control cables that are attached to the insertion tube's distal end and extend the length of the insertion tube. The control cables are directly connected to control wheels mounted to the handle portion. The control wheels are used to control articulation of the insertion tube by rotating the control wheels relative to the handle, thereby pulling directly on the control cables and causing the distal section of the insertion tube to bend. Accordingly, the insertion tube can be steered by a physician to follow the contours of a pathway through the patient's body to desired body cavity. The tip of the insertion tube must be accurately steerable in the up/down and left/right directions to permit the physician to place the tip at a selected location once the distal end of the insertion tube is within the selected body cavity.

The insertion tube of a conventional, non-sheathed endoscope includes a biopsy channel, suction channels, and air and water channels that extend along the length of the insertion tube. The insertion tube is axially rigid, yet sufficiently flexible to allow it to follow the curves and bends along the pathway in the patient; however, it must be sufficiently stiff in order to prevent the biopsy channel, the suction channel, or the air and water channels from collapsing when the insertion tube is articulated.

Improved endoscopes are used with an endoscopic sheath, as is described in U.S. Pat. No. 4,646,722, to Silverstein et al. The sheath covers and isolates the insertion tube from the contaminated environment. The sheath typically includes a plurality of integral channels, including a biopsy channel, a suction channel, and air and water channels. The endoscope sheath is sufficiently flexible to bend with the insertion tube while being stiff enough to prevent the channels from kinking or collapsing during articulation of the insertion tube.

It is especially important that the biopsy channel of the insertion tube or sheath not collapse or excessively narrow because an endoscopic accessory, such as a forceps or the like may be required to travel along the biopsy channel during an endoscopic procedure, or alternatively, it may be necessary to remove particulate matter from the tip of the endoscope through the biopsy channel. In addition, the endoscopic accessories further add to the overall stiffness of the sheathed or unsheathed insertion tube.

The necessary stiffness of the unsheathed or sheathed insertion tube results in a significant resistance to articulation of the insertion tube's distal end that is felt by the physician during manipulation of the control wheels. The resistance to articulation is overcome by exerting a significant amount of axial force on the selected control cables. Accordingly, a significant amount of force must be exerted by the physician on the conventional control wheels so as to sufficiently pull on one or more of the control cables to overcome the inherent resistance to bending.

During a clinical procedure the handle portion of the instrument is typically held in the physician's left hand. The right hand is usually placed on the endoscope's shaft to advance the instrument into the patient and to retract the instrument out of the patient. Preferably, the physician's right hand is not used to manipulate the control wheels in order to avoid contamination of the endoscope. Accordingly, the control wheels are adjusted with only one hand. The physical effort required to rotate the control wheels with one hand to overcome the stiffness of the insertion tube, sheath, and accessory can result in excessive fatigue of the physician's left hand, particularly during a long endoscopic procedure. The excessive effort required to articulate the insertion tube also greatly increases the duration of a procedure, thereby reducing the cost efficiency of the endoscopic procedure.

Conventional endoscopes have been designed to reduce the amount of effort required to move the control wheels by rigidly connecting a small diameter drum located within the handle portion to a large diameter control wheel that is rotated by the physician's thumb. The control cables extend around the small diameter drum so as to move axially when the drum is rotated. Although the combination of the large control wheel and smaller drum facilitates articulation of the insertion tube's distal end, the optimum size combination of control wheel and drum still requires a substantially large force to be exerted by the physician on the control wheels to achieve the necessary torque on the drum to steer or otherwise control the insertion tube's distal end.

There are other endoscopic devices which require the generation of a force at the distal tip of the device. A lithotripter is a basket device which is used to crush kidney or bile stones for removal. A conventional lithotripsy device uses a screw mechanism that is rotated at its proximal end in order to provide sufficient force at the distal end to crush the stones and facilitate their removal. The force required to turn the screw to generate the sufficient force to crush the kidney or bile stones is typically high enough that it is very difficult for the physician to maintain during the endoscopic procedure without mechanical advantage.

SUMMARY OF THE INVENTION

The present invention is directed toward an endoscope articulation system that reduces the amount of effort and force necessary for use of the control mechanism to articulate the distal end of an endoscopic device. In a preferred embodiment of the invention, an endoscopic device includes a handle and an insertion tube attached to the handle. The insertion tube has a distal section that is articulatable relative to a proximal section that engages the handle. At least one control cable is securely attached to the insertion tube's distal section, and the control cable extends proximally toward the handle. The control cable is axially movable relative to the insertion tube to cause the distal section of the insertion tube to articulate. A control member is movably attached to the handle and positioned for ease of manipulation by a user to control articulation of the distal section of the insertion tube. The control member is movable upon a first force being applied thereto by the user. The articulation system is connected to the control member and to the control cable. The articulation system includes a component that is substantially linearly movable relative to the control member so as to convert the first force, which is applied to the control member, into a second force that is exerted on the control cable, thereby causing the axial movement of the control cable and articulation of the distal section. The second force is greater than the first force, such that the articulation system provides a mechanical advantage between movement of the control member and axial movement of the control cable.

In the preferred embodiment, the control member includes a control wheel and drum assembly. The articulation system includes a movable pulley and connecting cable. The connecting cable extends around the movable pulley and around the drum. The movable pulley is securely connected to an end of the control cable, and the pulley is substantially linearly movable relative to the drum and control wheel upon rotation of the control wheel and drum. This configuration provides increased mechanical advantage between movement of the control member and axial movement of the control cables, with the result that a reduced force exerted by the physician or other user is needed at the control wheel in order to articulate and steer the distal end of the insertion tube.

In an alternate embodiment of the invention, the articulation system includes a lever that is pivotally mounted at a pivot point to the handle. The control cable is attached to a first portion of the lever at a first distance from the pivot point, such that pivotal movement of the lever results in substantially linear movement of the lever's first portion and axial movement of the control cable. A connecting member connects the lever to the drum and control wheel, such that rotation of the control wheel causes the lever to pivot relative to the handle, thereby causing the control cable to move axially. The connecting member is connected to the lever at a second distance from the pivot point that is different than the first distance, so the lever provides a mechanical advantage in transferring force from the control wheel to the control cable.

DETAILED DESCRIPTION OF THE INVENTION

Figure 1:
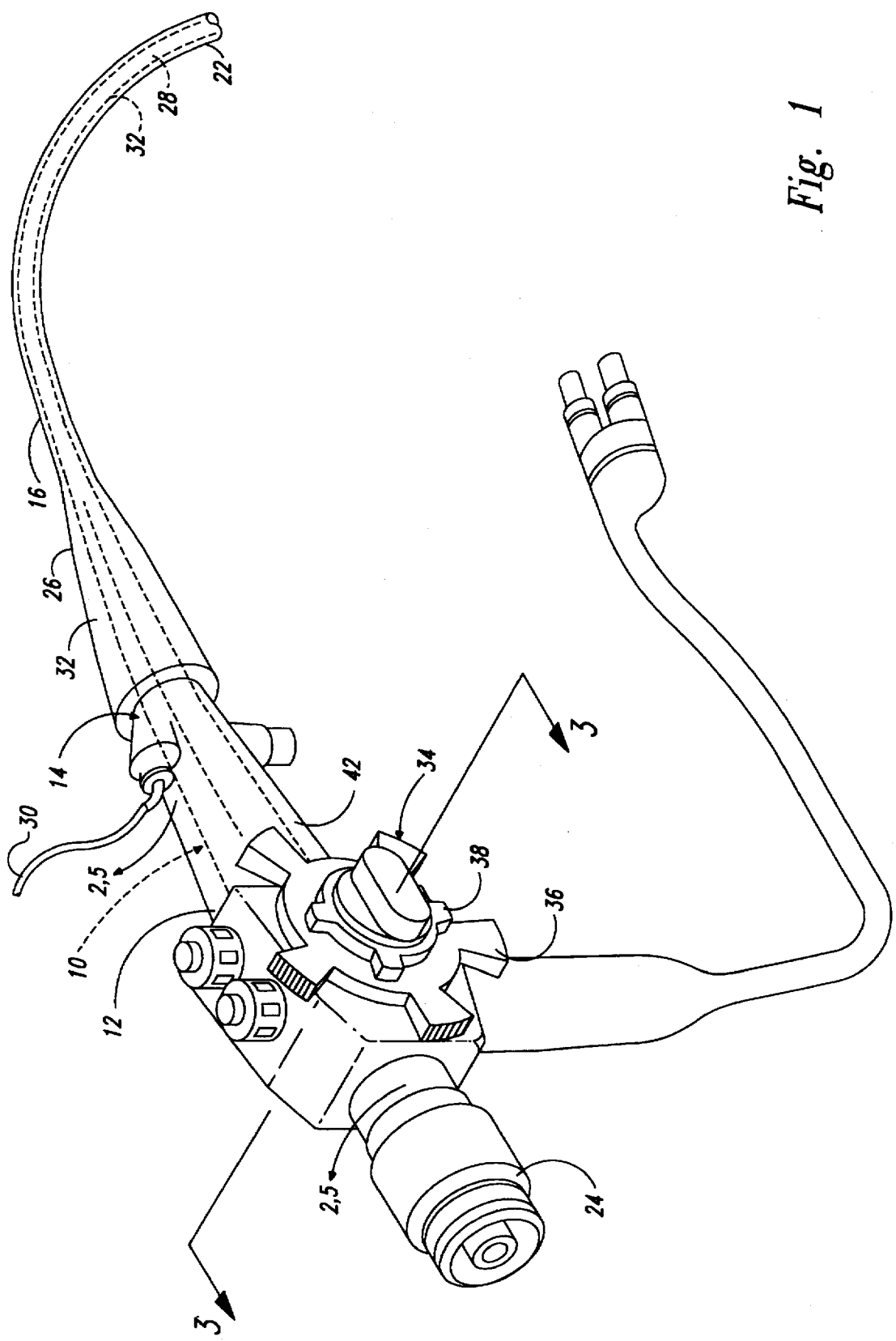
FIG. 1 is an isometric view of an endoscope and sheath assembly with an endoscope articulation system in accordance with the present invention contained within the handle of the endoscope.

As shown in FIG. 1, an articulation system 10 in accordance with a preferred embodiment of the invention is positioned within a handle 12 of a sheathed endoscope 14 that is used by a physician to perform endoscopic procedures. The endoscope 14 has an elongated insertion tube 16 connected at its proximal section 18 to the handle 12. A distal section 22 of the insertion tube 16, opposite the proximal section is shaped and sized to extend into a selected body cavity of a patient. As is well known in the art, the insertion tube 16 includes a device for conveying an image from the insertion tube's distal section 22 to an eyepiece 24 connected to the proximal end of the handle 12. A number of devices can be used to perform this function, including, for example, a lens that is optically coupled to the eyepiece through an optical waveguide, or a miniature camera that is electronically coupled to a monitor. The imaging device enables the physician to see portions of the patient's body cavity and to see objects located just beyond the distal section 22 of the insertion tube 16 during the endoscopic procedure.

The insertion tube 16 in the illustrated embodiment is removably positioned within an endoscopic sheath 26 to isolate the insertion tube from the contaminated environment during the endoscopic procedure. The sheath 26 has a plurality of channels extending along its length, including an endoscope channel that receives and isolates the insertion tube 16, air and water channels that direct air and water to the distal end of the insertion tube, a suction channel that provides a suction force at the insertion tube's distal end 22, and a biopsy channel 28 that slidably receives an endoscopic accessory 30 therein. The endoscopic accessory 30 typically includes an elongated, axially rigid shaft, such as a kink-resistant catheter, with a tool on the distal end that is passed through the biopsy channel 28 and beyond the open distal end of the biopsy channel to perform a selected endoscopic procedure that is viewed through the insertion tube 16 via the eyepiece 24.

The biopsy channel 28, the air and water channels, and the suction channel are flexible enough to bend when the insertion tube 16 articulates, but are sufficiently stiff to prevent kinking of the channels during the most extreme articulation. The stiffness of the channels of the sheath 26, the endoscopic accessory 30, and the insertion tube 16 combine to significantly resist articulation of the insertion tube's distal section 22.

The insertion tube 16 includes a plurality of control cables 32 that are securely attached to the distal section 22 of the insertion tube and extend proximally along the length of the insertion tube to the handle 12. The control cables 32 are axially movable within the insertion tube 16 except at their distal ends, such that the control cables cause the distal section 22 of the insertion tube to articulate in the up/down or left/right directions when a selected cable is moved axially.

A control mechanism 34 that includes two control wheels 36 and 38 is rotatably mounted on the handle 12 in a position that allows a physician to rotate the control wheels with his or her thumb while holding the handle with the same hand. The control wheels 36 and 38 are coupled to the control cables 32 by the articulation system 10, as discussed in detail below, such that rotation of one of the control wheels results in axial movement of at least one control cable, thereby articulating the distal section 22 of the insertion tube 16. The articulation system 10 provides a mechanical advantage between the control wheels 36 and 38 and the control cables 32 to reduce the amount of force needed to be exerted by the physician on the control wheels in order to articulate the insertion tube's distal section 22. Accordingly, the physician can easily control the position and degree of articulation of the distal section 22 and precisely position the distal end of the insertion tube for performing a selected diagnostic or therapeutic procedure without excess fatigue.

Figure 2:
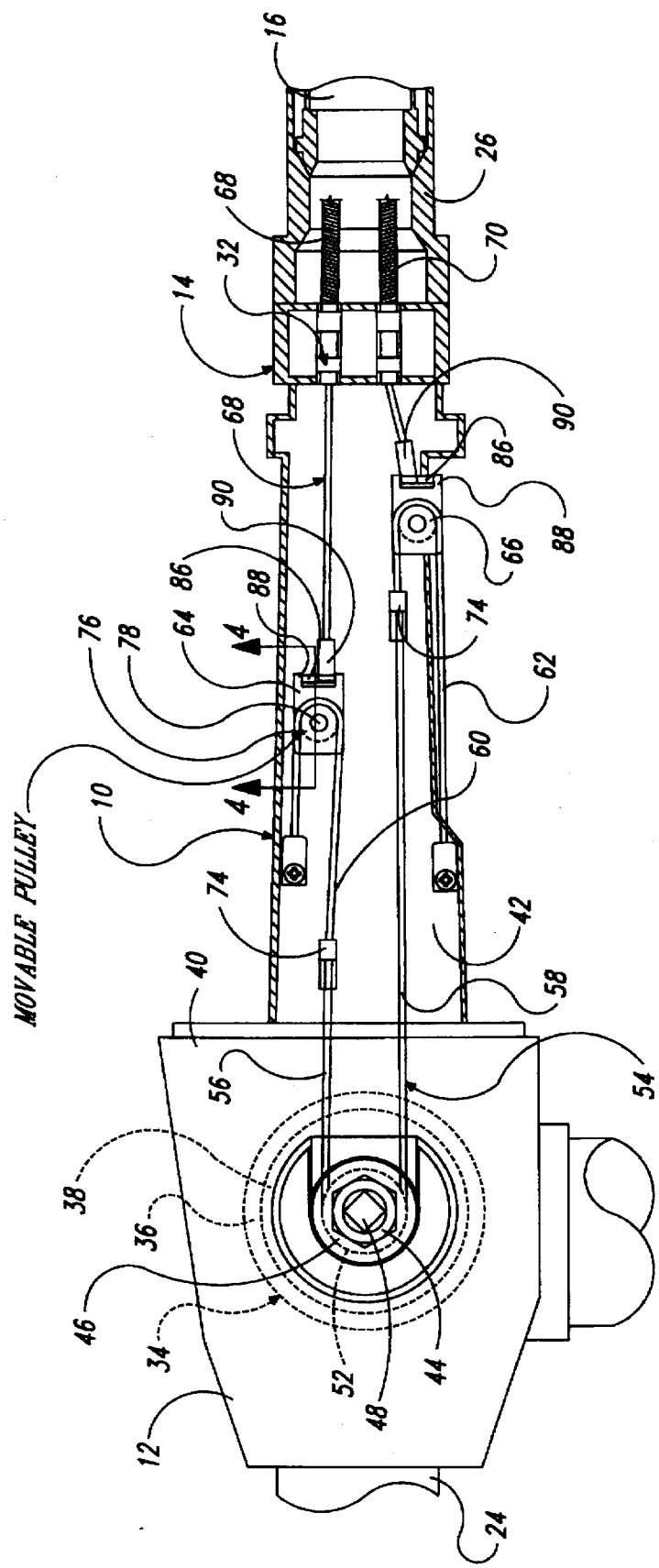
FIG. 2 is an enlarged cross-sectional view taken substantially along line 2—2 of FIG. 1 showing an embodiment of the endoscope articulation system within the handle of the endoscope.

As best seen in FIG. 2, the articulation system 10 is positioned within an interior chamber 40 defined by sidewalls 42 of the handle 12. The articulation system 10 is attached to the proximal ends of the control cables 32, which extend into the distal portion of the handle 12. The articulation system 10 extends between the proximal ends of the control cables 32 and the control mechanism 34 located at the proximal portion of the handle 12.

Figure 3:
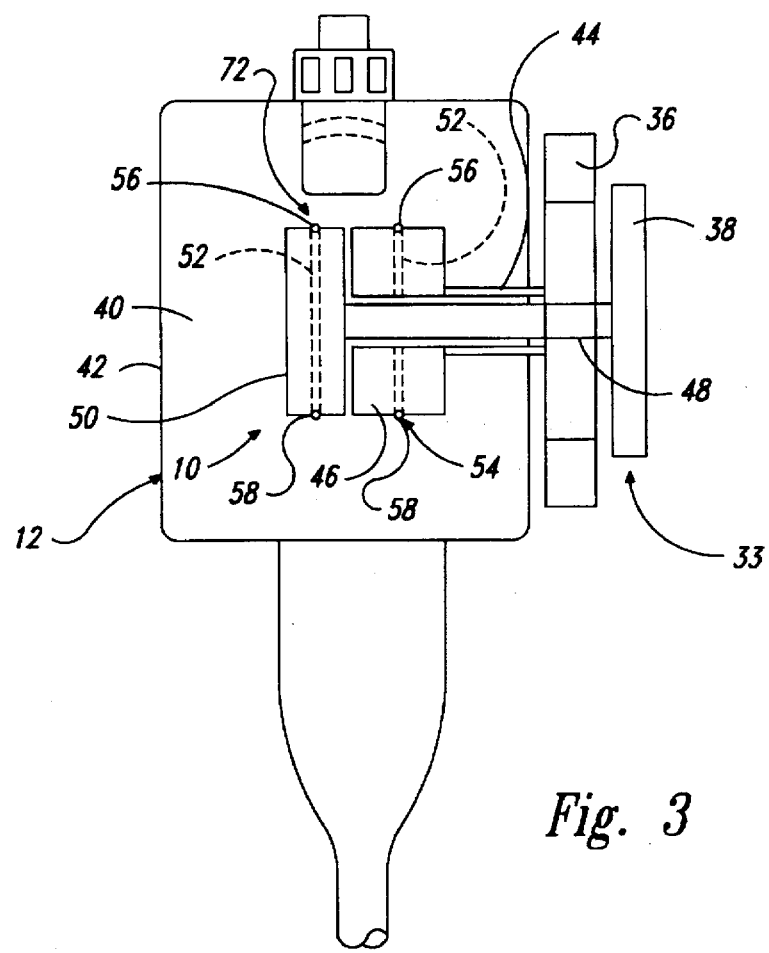
FIG. 3 is an enlarged cross-sectional view taken substantially along line 3—3 of FIG. 1 showing a control mechanism including exterior control wheels and interior drums mounted on the endoscope handle.

As best seen in FIG. 3, the control mechanism 34 includes an inner control wheel 36 rigidly connected to an exterior shaft 44 that extends through a sidewall 42 of the handle 12 and rigidly connects to a first coaxially aligned drum 46 within the interior chamber 40. The control mechanism 34 also includes an outer control wheel 38 rigidly connected to an interior shaft 48 that is positioned partially within the exterior shaft 44 and coaxially aligned with the inner control wheel 36 and the first drum 46. The interior shaft 48 extends through the inner control wheel 36, the exterior shaft 44, and the first drum 46, and rigidly connects to a second drum 50 adjacent to the first drum. Accordingly, the inner and outer control wheels 36 and 38 are independently rotatable relative to each other and relative to the handle 12 so as to independently rotate the first and second drums 46 and 50. The first and second drums 46 and 50 each have a diameter that is smaller than the diameter of their respective control wheels 36 and 38 in order to provide a first degree of mechanical advantage between the force exerted on the control wheel and the force transmitted by the drum.

The first and second drums 46 and 50 each have an annular groove 52 therearound that securely receives a control wire 54 of the articulation system 10, such that rotation of the first and second drums move their respective control wires around the drum without slippage. Accordingly, rotation of, for example, the inner control wheel 36 by a physician or other user causes the exterior shaft 44 to rotate which, in tin-n, causes the first drum 46 to rotate, thereby moving the control wire 54 around the first drum.

As best seen in FIG. 2, the control wire 54 has an upper section 56 that extends distally away from the top of the respective drum toward the control cables 32 and a lower section 58 that extends distally away from the bottom of the drum. The upper and lower sections 56 and 58 are integrally connected by the portion of the control wire 54 wrapped around the respective drum. The control wire 54 has a fixed length, such that when the control wheel 36 or 38 is rotated, the upper and lower sections 56 and 58 move axially in the opposite directions. In the preferred embodiment, the control wire 48 is a stainless steel cable, although other suitable materials can be used, and the drum and control wheel can be modified in order to maintain secure engagement with the control wire without slippage of the control wire over the drum.

Each control wire 54 is coupled to two of the control cables 32 by flexible connecting cable portions 60 and 62 and movable pulleys 64 and 66 of the articulation system 10. For purposes of simplicity, only one control wire 54 is illustrated in FIG. 2 being coupled to first and second control cables 68 and 70. The first control cable 68 controls upward articulation of the insertion tube's distal section 22, and the second control cable 70 controls downward articulation of the insertion tube's distal section. It is to be understood that, in the preferred embodiment, a second control wire 72, illustrated in FIG. 3, is coupled in the same manner to two similar control cables that control left and right articulation of the insertion tube's distal section.

The upper section 56 of the control wire 54 is securely connected at its distal end to a first end of the upper flexible cable portion 60 by a cable coupling device 74, so axial movement of the upper section causes axial movement in the upper flexible cable portion without any stretching of the flexible cable. The upper flexible cable portion 60 extends around an upper movable pulley 64 and is securely anchored at its second end to the sidewall 42 of the handle 12. The upper section 56 of the control wire 54 and the upper flexible cable portion 60 are pulled axially toward the first drum 46 when the control wheel 36 and first drum are rotated counterclockwise. Thus, the upper flexible cable portion 60 is pulled over the upper movable pulley and the upper movable pulley 64 is pulled substantially linearly and proximally away from the insertion tube 16. The proximal movement of the upper movable pulley 64 causes the first control cable 68 to move axially within the insertion tube 16 and to articulate the insertion tube's distal section upwardly.

Accordingly, the articulation system 10 transmits the rotational movement of the control wheels 36 and 38 to the axial movement of the control cables 32. The upper movable pulley 64 moves in a substantially linear direction relative to the control wheels 36 and the first drum 46, and provides a two-to-one mechanical advantage between the first control cable 68 and the control mechanism 34. As a result, the force exerted on the control wire 54 at the first drum 46 is approximately one-half of the axial force exerted by the upper movable pulley 64 on the first control cable 68. Thus, the articulation system 10 converts the first force exerted by a physician on a control wheel to the increased second force on the selected control cable to cause axial movement of the control cable and the articulation of the insertion tube's distal section. The articulation system 10 also allows for substantially reduced physical exertion by a physician in order to articulate and steer the distal section of the endoscope.

Similar to the control wife's upper section 56, the lower section 58 is rigidly connected to the first end of a lower flexible cable portion 62 that extends around the lower movable pulley 66 and is anchored at its second end to the handle's sidewall 42. The lower movable pulley 66 is securely connected to the second control cable 70. The lower movable pulley 66 moves in a substantially linear direction relative to the control mechanism 34, and provides a two-to-one mechanical advantage between the second control cable 70 and the control mechanism 34. Accordingly, the force exerted on the control wire 54 at the second drum 50 (FIG. 3) is approximately one-half of the axial force exerted on the second control cable.

The control wire 54 and the upper and lower cable portions 60 and 62 form a connecting cable 63 that extends around the movable pulleys 64 and 66 and that connects to the control mechanism 34. Accordingly, as shown in FIG. 2, the control cables 68 and 70 do not wrap around the movable pulleys 64 and 66.

In one embodiment of the invention, the upper and lower flexible cable portions 60 and 62 are constructed of a non-stretchable, fine, multi-strand metallic cable or, in the alternative, a non-metallic flexible material, such as oriented ultra-high molecular weight polyethylene. As indicated above, the upper and lower section 56 and 58 of the control wire 48 are integrally connected by the portion extending around the drum 46, such that the upper and lower sections, the upper and lower flexible cable portions 60 and 62, the upper and lower movable pulleys 64 and 66, and the respective first and second control cables 68 and 70 move simultaneously in opposite directions relative to the handle 12 when the inner control wheel 36 is rotated. A similar configuration is provided for the control cables that control left and right motion, such that rotation of the outer control wheel 38 and second drum 50 causes one movable pulley to move distally relative to the second drum as the other movable pulley moves proximally, thereby causing the distal section of the insertion tube to articulate either left or right.

Figure 4:
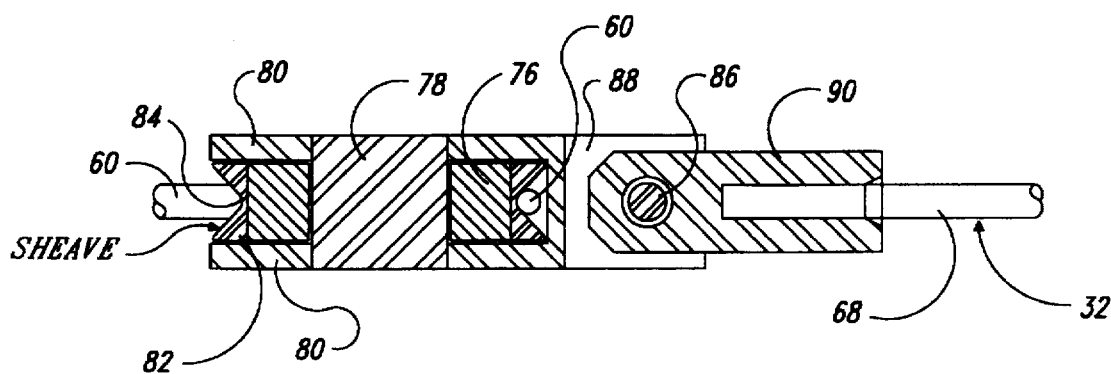
FIG. 4 is an enlarged cross-sectional view taken substantially along line 4—4 of FIG. 2 showing the movable pulley assembly of the endoscope articulation system.

As best seen in FIG. 4, the upper movable pulley 64 includes a pulley wheel 76 that is rotatably mounted on an axle 78 extending between two sideplates 80 that protect the pulley wheel. The pulley wheel 76 has an outer sheave 82 extending about its outer circumference. The outer sheave 82 has a groove 84 formed therein that is shaped to securely receive and grip the upper flexible cable portion 60 therein to prevent slippage as the flexible cable moves around the pulley wheel 76. The outer sheaf 82 also maintains the upper flexible cable portion 60 in a centered position around the pulley wheel 76. The movable pulley 64 further includes a pin 86 that extends between leg portions 88, shown in FIGS. 2 and 4, and the pin extends through a connection member 90 that is rigidly attached to the first control cable 70. The connection member 90 is allowed to move along the pin 86 between the leg portions 88 so the angular orientation of the first control cable 68 relative to the upper movable pulley 64 can change as the upper movable pulley and the first control cable move between distal and proximal positions within the handle 12. The pin 86 and connection member 90 arrangement effectively reduces the bending forces exerted on the proximal end of the first control cable 68 when the movable pulley and the control cable are in the distal-most position. The lower movable pulley 66 has configuration identical to the upper pulley 68, and the lower movable pulley is connected to the lower control cable with the same type of connection member 90.

Although the illustrated embodiment obtains a two-to-one mechanical advantage with a single movable pulley connected to each control cable, greater mechanical advantage can be achieved between the control wheel and each control cable by use of more than one pulley as in, for example, a block-and-tackle arrangement. The movable pulleys 66 and 68 of the illustrated articulation system 10 allow for the increased mechanical advantage with movable pulleys that are small enough to be contained and isolated within the confines of the handle's interior chamber 40. However, the movable pulleys do not have to be completely contained within the interior chamber.

While the arrangement can be used to improve mechanical advantage of a conventional, unsheathed endoscope design, it is especially important for non-conventional endoscope design, such as the flexible endoscope 14 illustrated in FIG. 1 that is used with the disposable sheath 26. In these non-conventional, non-symmetrical designs, the force required to articulate the distal section of the insertion tube is greater than the conventional endoscopes, because the stiffness of the disposable sheath is combined with the inherent stiffness of the endoscope, as discussed above.

Figure 5:
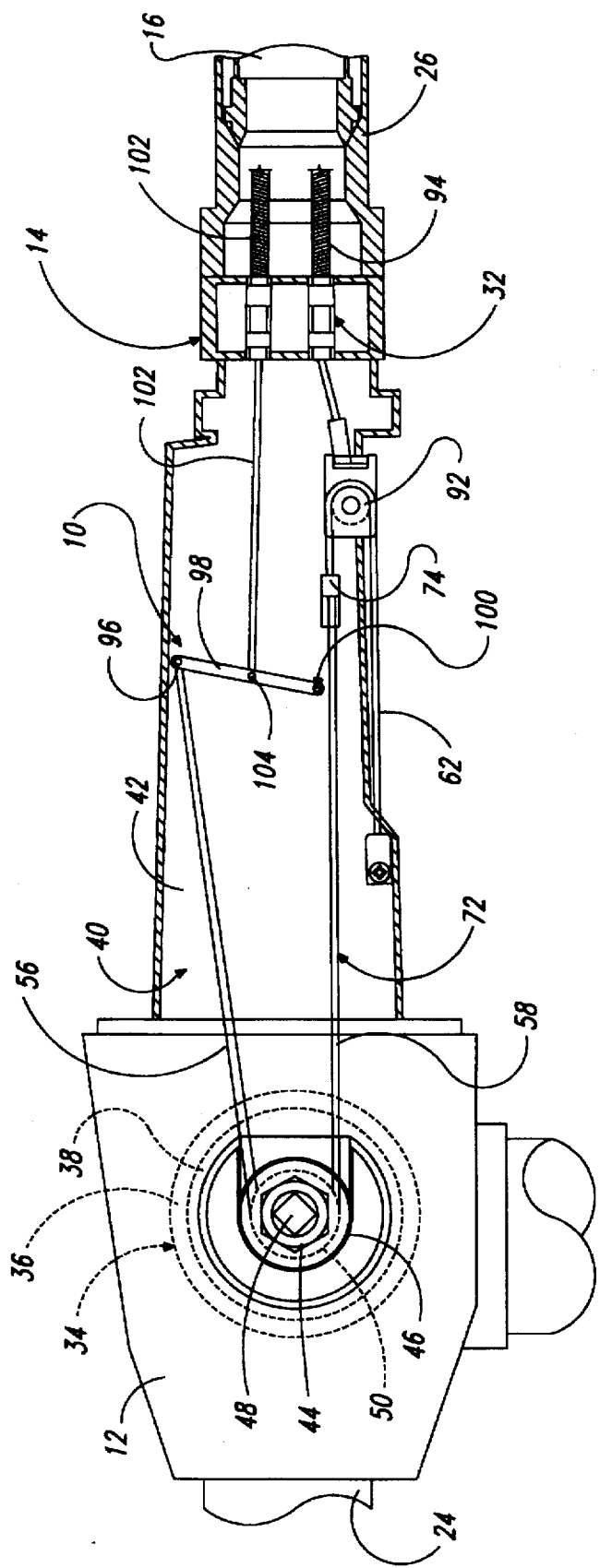
FIG. 5 is an enlarged cross-sectional view of an alternate embodiment of the endoscope articulation system in accordance with the present invention.

As best seen in FIG. 5, an alternate embodiment of the articulation system 10 is illustrated having a system utilizing a movable pulley 92, a lower flexible cable portion 62, and control cable 54 that are similar to the embodiment discussed above. The movable pulley 92 is securely connected to a left control cable 94 that controls articulation of the insertion tube's 16 distal section in the left direction. The upper section 56 of the control wire 54 extends distally away from the second drum 66 and connects at its distal end to an upper end 96 of a lever 98. The lever 98 is pivotally connected to the handle 12 within the interior chamber 40, and the lever pivots about a pivot point 100 that is at a first distance from the distal end of the control wire's upper section 56. When the outer control wheel 38 is rotated counterclockwise, the control wife's upper section 56 pulls the lever's upper end 96 substantially linearly and proximally through an arc, causing the lever to pivot about the pivot point 100. Conversely, when the outer control wheel 38 is rotated clockwise, the lever 98 pivots, such that the upper end 96 moves substantially linearly and distally through an arc.

The proximal end of the right control cable 102, which controls articulation of the insertion tube's distal section in the right direction, is securely connected to the lever 98 at a mid-point 104 between the lever's upper end 96 and the pivot point 100. In the illustrated embodiment, the distance from the pivot point 100 to the mid-point 104 is approximately half the distance between the distal end of the control wire's upper section 56 and the pivot point 100. When the outer control wheel 38 is rotated counterclockwise and the lever 98 pivots about the pivot point 100, the mid-point 104 moves proximally in a generally linear direction toward the control wheel, thereby pulling the right control cable 102 axially in the proximal direction. The lever 98 provides approximately a two-to-one mechanical advantage over a configuration with the control wire 54 directly attached to the right control cable 102. Accordingly, a first amount of force exerted on the control wire via the outer control wheel 38 results in a second force that is twice the first force and that is exerted axially on the right control cable 102. Thus, the lever 98 and control wire 54 work together to transmit the rotational movement of the outer control wheel 38 to the axial movement of the control cable 102. The lever 98 and control wire 54 also work together to convert the first force exerted by the physician on the control wheel 38 to the increased second force exerted on the right control cable 102 to cause axial movement of the control cable and articulation of the insertion tube's distal section.

This increased mechanical advantage allows the physician to easily articulate the distal section of the insertion tube with a reduced effort, as discussed above. Although the illustrated alternate embodiment shows the lever providing a two-to-one mechanical advantage, other alternate embodiments can have the connection point of the control cable at a position along the length of the lever other than the mid-point to increase or decrease the mechanical advantage as desired. In addition, the illustrated alternate embodiment has the lever 98 used in conjunction with a lower movable pulley 66, although the lower movable pulley may also be replaced by a similar lever mechanism to provide the increased mechanical advantage between the control mechanism and control cable. Further, it is to be understood that either a lever assembly, a movable pulley, or other mechanical advantage coupler in accordance with the present invention can be connected to the upper, lower, left, or right control cables to provide the increased mechanical advantage.

Numerous modifications and variations of the endoscope articulation system to reduce effort during articulation of an endoscope invention disclosed herein will occur to those skilled in the art in view of this disclosure. Other types of devices that provide mechanical advantage between the control wheel and the control cable can be used while remaining within the spirit and scope of the present invention. Therefore, it is to be understood that these modifications and variations, and equivalents thereof, may be practiced while remaining within the spirit and the scope of the invention as defined in the following claims.

We claim:

1. An endoscope, comprising:

a handle;

an insertion tube having a proximal section attached to said handle and having a distal section opposite said proximal section, said distal section being articulatable relative to said proximal section;

a control cable attached to said distal section of said insertion tube, said control cable being axially movable relative to said insertion tube, said distal section of said insertion tube being articulated upon axial movement of said control cable;

a control member attached to said handle and positioned for movement by a user relative to said handle; and a mechanical advantage coupler connected to said control member and to said control cable, said mechanical advantage coupler having a component that is substantially linearly movable relative to said control member, said mechanical advantage coupler providing a mechanical advantage between said movement of said control member and axial movement of said control cable, said mechanical advantage coupler includes a pulley assembly connected to said control cable and coupled to said control member, said pulley assembly including a pulley wheel and cable portion extending around said pulley wheel, said cable portion being attached to said control member and being movable over said pulley wheel upon movement of said control member.

2. The endoscope of claim 1 wherein said handle includes a housing that defines an interior chamber, and said movable pulley is positioned within said interior chamber between said control member and said control cable.

3. The endoscope of claim 1 wherein said mechanical advantage coupler includes a lever and a connecting member, said lever being pivotally mounted at a pivot point to said handle, said control cable being attached to a first portion of said lever at a first distance from said pivot point, said first portion of said lever being substantially linearly movable relative to said control member, said connecting member being connected to said control member and connected to a second portion of said lever a second distance from said pivot point, said second distance being different than said first distance.

4. The endoscope of claim 1 wherein said mechanical advantage coupler includes a lever and a connecting member, a first portion of said lever being connected to said handle and a second portion of said lever being connected to said control cable, said second portion of said lever being substantially linearly movable relative to said control member, and said connecting member having a first end connected to said lever and a second end connected to said control member.

5. The endoscope of claim 1 wherein said axial movement of said control cable articulates said distal section of said insertion tube in a first plane of movement, and further comprising:

a second control cable attached to said distal section of said insertion tube, said second control cable being axially movable relative to said insertion tube to cause said distal section of said insertion tube to articulate in a second plane of movement that is different than said first plane of movement;

a second control member attached to said handle and positioned for movement by a user relative to said handle; and a second mechanical advantage coupler connected to said second control member and attached to said second control cable, said second mechanical advantage coupler having a component that is substantially linearly movable relative to said second control member, said second mechanical advantage coupler providing a mechanical advantage between movement of said second control member and movement of said second control cable.

6. The endoscope of claim 5 wherein said second mechanical advantage coupler includes a second pulley assembly connected to said second control cable and coupled to said control member, said second pulley assembly including a second pulley wheel and a second cable portion extending around said second pulley wheel, said second cable portion being attached to said second control member and being movable over said second pulley wheel upon movement of said control member.

7. The endoscope of claim 5 wherein said second mechanical advantage coupler includes a second lever and a second connecting member, said second lever having a third portion connected to said handle and having a fourth portion connected to said second control cable, said fourth portion of said second lever being substantially linearly movable relative to said second control member, and said second connecting member being connected to said second lever and to said second control member.

8. An endoscope, comprising:

a handle adapted to be held by a user during an endoscopic procedure;

an insertion tube having proximal and distal sections, said proximal section being attached to said handle and said distal section being opposite said proximal section and being articulatably movable relative to said proximal section;

a control cable attached to said distal section of said insertion tube and being axially movable relative to said insertion tube to cause said distal section of said insertion tube to articulate;

a control member attached to said handle and adapted to control articulation of said distal section, said control member being movable by a user relative to said handle during the endoscopic procedure; and a transmitting means connected at a first portion to said control cable and connected at a second portion to said control member, said transmitting means being configured to transmit movement of said control member to said control cable to cause axial movement of said control cable to articulate said distal end of said insertion tube, said transmitting means being substantially linearly movable relative to said control member and relative to said control cable, said transmitting means providing a mechanical advantage in transmitting said movement of said control member to said control cable for articulation of said distal section, said transmitting means includes a movable pulley and a connecting cable extending around the movable pulley, said movable pulley being connected to said control cable and being movable over said connecting cable, said connecting cable being attached to said movable pulley and to said control member.

9. The endoscope of claim 8 wherein said handle includes a housing that defines an interior chamber, and said movable pulley is positioned within said interior chamber between said control member and said control cable.

10. The endoscope of claim 8 wherein said transmitting means includes a lever and a connecting member, said lever being pivotally mounted at a pivot point to said handle, said control cable being attached to a first portion of said lever at a first distance from said pivot point, said first portion of said lever being substantially linearly movable relative to said control member, said connecting member having first and second ends with said first end connected to a second portion of said lever a second distance from said pivot point, said second distance being different than said first distance, and said second end of said connecting member being connected to said control member.

11. The endoscope of claim 8 wherein said transmitting means includes a lever and a connecting member, a first portion of said lever being connected to said handle and a second portion of said lever being connected to said control cable, said second portion of said lever being substantially linearly movable relative to said control member and said connecting member having a first end connected to said lever and a second end connected to said control member.

12. The endoscope of claim 8 wherein said axial movement of said control cable articulates said distal section of said insertion tube in a first plane of movement and said control member has first and second portions, said first portion being connected to said first transmitting means, and said second portion being movable relative to said handle, and the endoscope further comprising:

a second control cable attached to said distal section of said insertion tube, said second control cable being axially movable relative to said insertion tube to cause said distal section of said insertion tube to articulate in a second plane of movement that is different than said first plane; and a second transmitting means connected to said second control cable and connected to said second portion of said control member, said second transmitting means transmitting movement of said second portion of said control member to said second control cable to cause axial movement of said second control cable and articulation of said distal section, said second transmitting means having a component that is substantially linearly movable relative to said control member and relative to said second control cable, said second transmitting means providing mechanical advantage in transmitting said movement of said second portion of said control member to said second control cable for articulation of said distal section in said second plane of movement.

13. The endoscope of claim 12 wherein said second transmitting means includes a lever and a connecting member, said lever being pivotally mounted at a pivot point to said handle, said second control cable being attached to a first portion of said lever at a first distance from said pivot point, said first portion of said lever being substantially linearly movable relative to said control member, said connecting member being connected to said second portion of said control member and being connected to a second portion of said lever a second distance from said pivot point, said second distance being different than said first distance.

14. An endoscope assembly usable for an endoscopic procedure, comprising:

a handle having a housing defining an interior chamber with proximal and distal ends;

an insertion tube having proximal and distal sections, said proximal section attached to said housing at said distal end of said interior chamber and said distal section being opposite said proximal section and articulatable relative to said proximal section;

a control cable attached to said distal section of said insertion tube for articulating said distal section in a plane of movement, said control cable extending proximally from said distal section toward said housing and terminating at a proximal end within said interior chamber;

a control member rotatably attached to said handle housing, said control member including a control wheel connected to a shaft and a drum connected to the shaft, said drum positioned within said interior chamber and said control wheel being exterior of said interior chamber and positioned to be rotated by a user holding onto said handle during the endoscopic procedure and exerting a first force on said control wheel, such that rotation of said control wheel relative to said housing causes said drum to rotate; and a connecting means securely connected to said proximal end of said control cable and to said drum, said connecting means being positioned within said interior chamber and having a component that is substantially linearly movable between said drum and said control cable, said connecting means transmitting movement of said control wheel and said drum to said control cable, and said connecting means converting said first force causing said rotational movement of said drum to a second force that causes axial movement of said control cable and articulating movement of said distal end and providing a mechanical advantage between first and second forces, said connecting means comprises a flexible cable connected to said drum and a pulley connected to said proximal end of said control cable, said flexible cable having first and second ends anchored to said housing and a middle portion therebetween that wraps partially around said drum and that wraps partially around said pulley, said pulley being substantially linearly movable relative to said drum upon rotation of said drum to cause said control cable to move axially.

15. The endoscopic assembly of claim 14 wherein said connecting means comprises a connecting cable connected to said drum and a lever pivotally mounted at a pivot point to said housing, said control cable being attached to a first portion of said lever at a first distance from said pivot point, said first portion of said lever being substantially linearly movable relative to said control member, said connecting cable having a first end connected to a second portion of said lever a second distance from said pivot point, said second distance being different than said first distance.

16. The endoscope assembly of claim 14 wherein said axial movement of said control cable articulates said distal section of said insertion tube in a first plane of movement, said control member including a second control wheel connected to a second shaft and a second drum connected to said second shaft, said second control wheel and said second drum being rotatable relative to said handle independent of said first control wheel and said first drum, said second control wheel being rotatable upon a third force being exerted thereon, and the endoscope assembly further comprising:

a second control cable attached to said distal section of said insertion tube for articulating said distal section in a second plane of movement that is different than said first plane, said second control cable extending proximally from said distal end toward said housing and terminating at a proximal end within said interior chamber; and a second connecting means securely connected to said proximal end of said second control cable and to said second drum, said second connecting means being positioned within said interior chamber and having a component that is substantially linearly movable between said second drum and said second control cable, said second connecting means transmitting movement of said second control wheel and said second drum to said second control cable, and said second connecting means converting said third force causing said rotational movement of said second drum to a fourth force that causes axial movement of said second control cable and articulating movement of said distal section in said second plane of movement and providing mechanical advantage between said third and fourth forces.

17. The endoscopic assembly of claim 16 wherein said second connecting means comprises said second flexible cable connected to said second drum and a lever pivotally mounted at a pivot point to said housing, said second control cable being attached to a first portion of said lever at a first distance from said pivot point, said first portion of said lever being substantially linearly movable relative to said control member, said second flexible cable being connected to a second portion of said lever a second distance from said pivot point, said second distance being different than said first distance.

18. An endoscope usable for an endoscopic procedure, comprising:
- a handle for holding during the endoscopic procedure, said handle having a housing defining an interior chamber;
- an insertion tube having a proximal end attached to said handle and a distal end opposite said proximal end, said insertion tube having an articulating section adjacent to said distal end that is articulatably movable in two planes, a plurality of interior control channels extending between the proximal and distal ends, said proximal end of said interior control channels coupled to said interior chamber;
- a plurality of control cables positioned within said plurality of interior control channels, said control cables having a proximal end and a distal end, said distal end being rigidly attached to said articulating section, each of said control cables being axially movable within a respective one of said interior control channels to cause said articulating section to articulate in at least one of the two planes;
- a control wheel assembly rotatably mounted to said handle, said control wheel having a shaft rotatably extending through a portion of said housing, said shaft having an interior end within said interior chamber and an exterior end exterior of said interior chamber, said control wheel further having an exterior control member and an interior control drum, said exterior control member being rigidly attached to said exterior end of said shaft and being adapted to be engaged by a user and rotated relative to said housing, and said interior control drum being rigidly attached to said interior end of said shaft and being rotatable relative to said housing upon rotation of said exterior control member; and
- a movable pulley system connected to said interior control drum and to said control cables, said movable pulley system including:
  - a control wire having first and second ends and a first middle portion extending therebetween, said first middle portion being movably wrapped around said interior control drum for axial movement upon rotation of said exterior control member;
  - a first flexible cable having a first anchored end rigidly anchored to said housing between said control wheel assembly and said proximal ends of said control cables, a first movable end rigidly connected to said first end of said control wire, and a second middle portion extending between said first anchored and movable ends;
  - a second flexible cable having a second anchored end rigidly anchored to said housing between said control wheel assembly and said proximal ends of said control cables, a second movable end rigidly connected to said second end of said control wire, and a third middle portion extending between said second anchored and movable ends;
  - a first movable pulley slidably attached to said proximal end of one of said control cables and movably attached to said second middle portion of said first flexible cable, such that said rotation of said exterior control wheel in a first direction rotates said interior control drum, thereby axially moving said first movable end and said second middle portion of said first flexible cable to cause said first movable pulley to move within said interior chamber thereby axially moving said one of said control cables and causing said distal end of said one of said control cables to pull on said articulating section of said insertion tube to articulate said articulating section in one of said two planes, said first movable pulley including an outer housing having a shaft extending therethrough and a first pulley wheel rotatably mounted on said shaft within said outer housing, said first pulley wheel engaging said second middle portion of said first flexible cable with the second middle portion extending around said first pulley wheel, and a retaining pin rigidly attached to said outer housing and slidably retaining said proximal end of said one of said control cables thereon, thereby providing a mechanical advantage within said interior chamber to articulate said articulating section; and
  - a second movable pulley slidably attached to said proximal end of a second of said control cables and movably attached to said third middle portion of said second flexible cable, such that said rotation of said exterior control wheel in a second direction rotates said interior control drum, thereby axially moving said second movable end and said third middle portion of said second flexible cable to cause said second movable pulley to move within said interior chamber thereby axially moving said second of said control cables and causing said distal end of said control cable to articulate said articulating end of said insertion tube in one of said two planes, said second movable pulley including an outer housing having a shaft extending therethrough and a second pulley wheel rotatably mounted on said shaft within said outer housing, said second pulley wheel engaging said third middle portion of said second flexible cable with the third middle portion extending around the second pulley wheel, and a retaining pin rigidly attached to said outer housing and slidably retaining said proximal end of said second one of said control cables thereon, thereby providing a mechanical advantage within said interior chamber to articulate said articulating section.

* * * * *